(12) United States Patent
Goddard et al.

(10) Patent No.: US 8,263,407 B2
(45) Date of Patent: Sep. 11, 2012

(54) METHOD FOR NON-CONTACT PARTICLE MANIPULATION AND CONTROL OF PARTICLE SPACING ALONG AN AXIS

(75) Inventors: Gregory Russ Goddard, Los Alamos, NM (US); Gregory Kaduchak, Eugene, OR (US); James Hubert Jett, Albuquerque, NM (US); Steven Wayde Graves, San Juan Pueblo, NM (US)

(73) Assignee: Los Alamos National Security, LLC, Los Alamos, NM (US)

( * ) Notice: Subject to any disclaimer, the term of this patent is extended or adjusted under 35 U.S.C. 154(b) by 223 days.

(21) Appl. No.: 12/288,896

(22) Filed: Oct. 23, 2008

(65) Prior Publication Data

US 2009/0139332 A1    Jun. 4, 2009

Related U.S. Application Data

(63) Continuation-in-part of application No. 11/923,403, filed on Oct. 24, 2007.

(51) Int. Cl.
   *G01N 33/48* (2006.01)
(52) U.S. Cl. ....... 436/63; 73/61.75; 73/64.53; 73/570.5; 73/865.5; 210/748.01
(58) Field of Classification Search .................. None
   See application file for complete search history.

(56) References Cited

U.S. PATENT DOCUMENTS

| | | |
|---|---|---|
| 3,882,732 A | 5/1975 | Fletcher et al. |
| 4,055,491 A | 10/1977 | Porath-Furedi |
| 4,265,124 A | 5/1981 | Lim et al. |
| 4,285,810 A | 8/1981 | Kirkland et al. |
| 4,350,683 A | 9/1982 | Galfre et al. |
| 4,434,230 A | 2/1984 | Ritts, Jr. |
| 4,492,752 A | 1/1985 | Hoffman et al. |
| 4,523,682 A | 6/1985 | Barmatz et al. |
| 4,523,982 A | 6/1985 | Lee |
| 4,604,542 A | 8/1986 | Thompson |
| 4,673,512 A | 6/1987 | Schram |
| 4,743,361 A | 5/1988 | Schram |
| 4,759,775 A | 7/1988 | Peterson et al. |
| 4,777,823 A | 10/1988 | Barmatz et al. |

(Continued)

FOREIGN PATENT DOCUMENTS

CN    1493831 A    5/2004

(Continued)

OTHER PUBLICATIONS

Neild, Adrian, A micro-particle positioning technique combining an ultrasonic manipulator and a microgripper, 2006, Journal of micromechanical microengineering, vol. 16, pp. 1562-1570.

(Continued)

*Primary Examiner* — Arlen Soderquist
*Assistant Examiner* — Robert Xu
(74) *Attorney, Agent, or Firm* — Woodcock Washburn, LLP

(57) ABSTRACT

Method and system for uniformly spacing particles in a flowing system comprising suspending particles in an elongated fluid filled cavity; exposing said cavity to an axial acoustic standing wave field, wherein said axial acoustic standing wave field drives said particles to nodal and anti-nodal positions along the center axis of said cavity to result in uniformly spaced particles; and focusing said particles to the center axis of said cavity.

10 Claims, 9 Drawing Sheets

U.S. PATENT DOCUMENTS

| | | | |
|---|---|---|---|
| 4,845,025 A | 7/1989 | Lary et al. |
| 4,867,559 A | 9/1989 | Bach |
| 4,877,516 A | 10/1989 | Schram |
| 4,913,883 A | 4/1990 | Imai et al. |
| 4,964,303 A | 10/1990 | Barmatz et al. |
| 4,979,824 A | 12/1990 | Mathies et al. |
| 4,987,086 A | 1/1991 | Brosnan et al. |
| 5,006,266 A | 4/1991 | Schram |
| 5,030,002 A | 7/1991 | North, Jr. |
| 5,032,381 A | 7/1991 | Bronstein et al. |
| 5,040,890 A | 8/1991 | North, Jr. |
| 5,079,959 A | 1/1992 | Miyake et al. |
| 5,085,783 A | 2/1992 | Feke et al. |
| 5,164,094 A | 11/1992 | Stuckart |
| 5,225,089 A | 7/1993 | Benes et al. |
| 5,346,670 A | 9/1994 | Renzoni et al. |
| 5,376,551 A | 12/1994 | Yoshikami |
| 5,395,588 A | 3/1995 | North, Jr. et al. |
| 5,430,541 A | 7/1995 | Sapp |
| 5,491,344 A | 2/1996 | Kenny et al. |
| 5,504,337 A | 4/1996 | Lakowicz et al. |
| 5,527,460 A | 6/1996 | Trampler et al. |
| 5,528,045 A | 6/1996 | Hoffman et al. |
| 5,547,849 A | 8/1996 | Baer et al. |
| 5,626,767 A | 5/1997 | Trampler et al. |
| 5,644,388 A | 7/1997 | Maekawa et al. |
| 5,674,698 A | 10/1997 | Zarling et al. |
| 5,688,406 A | 11/1997 | Dickinson et al. |
| 5,690,895 A | 11/1997 | Matsumoto et al. |
| 5,711,888 A | 1/1998 | Trampler et al. |
| 5,739,902 A | 4/1998 | Gjelsnes et al. |
| 5,798,222 A | 8/1998 | Goix |
| 5,800,861 A | 9/1998 | Chiang et al. |
| 5,831,166 A | 11/1998 | Kozuka et al. |
| 5,981,180 A | 11/1999 | Chandler et al. |
| 6,003,388 A | 12/1999 | Oeftering |
| 6,055,859 A | 5/2000 | Kozuka et al. |
| 6,074,879 A | 6/2000 | Zelmanovic et al. |
| 6,090,295 A | 7/2000 | Raghavarae et al. |
| 6,197,593 B1 | 3/2001 | Deka et al. |
| 6,216,538 B1 | 4/2001 | Yasuda et al. |
| 6,221,258 B1 * | 4/2001 | Feke et al. ............ 210/748 |
| 6,248,590 B1 | 6/2001 | Malachowski |
| 6,255,118 B1 | 7/2001 | Alfano et al. |
| 6,309,886 B1 | 10/2001 | Ambrose et al. |
| 6,332,541 B1 | 12/2001 | Coakley et al. |
| 6,348,687 B1 | 2/2002 | Brockmann et al. |
| 6,373,567 B1 | 4/2002 | Wise et al. |
| 6,449,563 B1 | 9/2002 | Dukhin et al. |
| 6,467,350 B1 | 10/2002 | Kaduchak et al. |
| 6,549,275 B1 | 4/2003 | Cabuz et al. |
| 6,565,727 B1 | 5/2003 | Shenderov et al. |
| 6,592,821 B1 | 7/2003 | Wada et al. |
| 6,604,435 B2 | 8/2003 | Buchanan et al. |
| 6,644,118 B2 | 11/2003 | Kaduchak et al. |
| 6,647,739 B1 | 11/2003 | Kim |
| 6,683,314 B2 | 1/2004 | Oostman, Jr. et al. |
| 6,713,019 B2 | 3/2004 | Ozasa et al. |
| 6,736,904 B2 | 5/2004 | Poniatowski et al. |
| 6,773,556 B1 | 8/2004 | Brockie et al. |
| 6,797,158 B2 | 9/2004 | Feke et al. |
| 6,813,017 B1 | 11/2004 | Hoffman et al. |
| 6,816,257 B2 | 11/2004 | Goix |
| 6,831,279 B2 | 12/2004 | Ho |
| 6,881,314 B1 | 4/2005 | Wang et al. |
| 6,929,750 B2 | 8/2005 | Laurell et al. |
| 7,008,540 B1 | 3/2006 | Weavers et al. |
| 7,018,819 B2 | 3/2006 | Orwar et al. |
| 7,047,809 B2 | 5/2006 | Cobb |
| 7,052,864 B2 | 5/2006 | Durkop et al. |
| 7,081,192 B1 | 7/2006 | Wang et al. |
| 7,108,137 B2 | 9/2006 | Lal et al. |
| 7,113,266 B1 | 9/2006 | Wells |
| 7,161,665 B2 | 1/2007 | Johnson |
| 7,255,780 B2 | 8/2007 | Shenderov |
| 7,262,838 B2 | 8/2007 | Fritz |
| 7,315,357 B2 | 1/2008 | Ortyn et al. |
| 7,329,545 B2 | 2/2008 | Pamula et al. |
| 7,362,432 B2 | 4/2008 | Roth |
| 7,373,805 B2 | 5/2008 | Hawkes et al. |
| 7,403,125 B2 | 7/2008 | Rich |
| 7,431,892 B2 | 10/2008 | Zumeris et al. |
| 7,477,363 B2 | 1/2009 | Nagai |
| 7,570,676 B2 | 8/2009 | Essaian et al. |
| 2003/0059850 A1 | 3/2003 | Evans |
| 2005/0072677 A1 | 4/2005 | Gascoyne et al. |
| 2006/0021437 A1 | 2/2006 | Kaduchak et al. |
| 2006/0034733 A1 | 2/2006 | Ferren et al. |
| 2006/0163166 A1 | 7/2006 | Hawkes et al. |
| 2007/0037172 A1 | 2/2007 | Chiu et al. |
| 2007/0071683 A1 | 3/2007 | Dayton et al. |
| 2007/0098232 A1 | 5/2007 | Matula et al. |
| 2007/0119239 A1 | 5/2007 | Priev et al. |
| 2008/0053787 A1 | 3/2008 | Bagajewicz |
| 2008/0106736 A1 | 5/2008 | Graves et al. |
| 2008/0245709 A1 | 10/2008 | Kaduchak et al. |
| 2008/0245745 A1 | 10/2008 | Ward et al. |
| 2009/0029870 A1 | 1/2009 | Ward et al. |
| 2009/0042239 A1 | 2/2009 | Ward et al. |
| 2009/0042310 A1 | 2/2009 | Ward et al. |
| 2009/0045107 A1 | 2/2009 | Ward et al. |
| 2009/0048805 A1 | 2/2009 | Kaduchak et al. |
| 2009/0050573 A1 | 2/2009 | Ward et al. |
| 2009/0053686 A1 | 2/2009 | Ward et al. |
| 2009/0107241 A1 | 4/2009 | Goddard et al. |
| 2009/0158823 A1 | 6/2009 | Kaduchak et al. |
| 2009/0162887 A1 | 6/2009 | Kaduchak et al. |
| 2009/0178716 A1 | 7/2009 | Kaduchak et al. |
| 2009/0227042 A1 | 9/2009 | Gauer et al. |
| 2009/0316151 A1 | 12/2009 | Matula et al. |
| 2010/0000325 A1 | 1/2010 | Kaduchak et al. |
| 2010/0009333 A1 | 1/2010 | Auer |
| 2011/0024335 A1 | 2/2011 | Ward et al. |
| 2011/0032522 A1 | 2/2011 | Graves et al. |
| 2011/0134426 A1 | 6/2011 | Kaduchak et al. |

FOREIGN PATENT DOCUMENTS

| | | |
|---|---|---|
| CN | 1739020 A | 2/2006 |
| DE | 3027433 | 2/1982 |
| EP | 0147032 | 3/1985 |
| EP | 0292470 | 11/1988 |
| EP | 0773055 | 5/1997 |
| EP | 1 416 239 | 5/2004 |
| FR | 821419 | 12/1937 |
| GB | 500271 | 12/1937 |
| JP | 363139231 | 6/1988 |
| JP | 01-112161 | 4/1989 |
| JP | 406241977 | 9/1994 |
| JP | 408266891 | 10/1996 |
| JP | 11-014533 | 1/1999 |
| RU | 2224992 | 2/2004 |
| WO | WO 88/09210 | 12/1988 |
| WO | WO 90/05008 | 5/1990 |
| WO | WO 94/29695 | 12/1994 |
| WO | WO 97/02482 | 1/1997 |
| WO | WO 99/42810 | 8/1999 |
| WO | WO 00/41794 | 7/2000 |
| WO | WO 02/059577 | 8/2002 |
| WO | WO 02/072234 | 9/2002 |
| WO | WO 02/072236 | 9/2002 |
| WO | WO 03/079006 | 9/2003 |
| WO | WO 2004/024287 | 3/2004 |
| WO | WO 2004/033087 | 4/2004 |
| WO | WO 2004/048948 | 6/2004 |
| WO | WO 2006/076195 | 7/2006 |
| WO | WO 2007/128795 | 11/2007 |
| WO | WO 2008/122051 | 10/2008 |
| WO | WO 2009/091925 | 7/2009 |
| WO | WO 2011/068764 | 6/2011 |

OTHER PUBLICATIONS

Aboobaker, et al., "Mathematical modeling of the movement of suspended particles subjected to acoustic and flow fields", App. Math. Modeling, 2005, 29, 515-532.

Anderson, et al., "The Physics and Technology of Ultrasonic Particle Separation in Air", WCU, 2003, 1615-1621.

Apfel, et al., "Acoustic Radiation Pressure—Principles and Application to Separation Science", Fortschritte Der Akustik DAGA '90, 1990, 19-30.

Araz, et al., "Ultrasonic Separation in Microfluidic Capillaries", IEEE Ultrasonics Symposium, 2003, 1066-1069.

Asai, et al., "Ultrasonic treatment of slurry", Third International Coal Preparation Conference, 1958, 518-527.

Bardsley, et al., "Electroacoustic Productions of Murine Hybridomas," Journal of Immunological Methods, 129(1), (no month available) 1990, pp. 41-47.

Barmatz, et al., "Acosutic radiation potential on a sphere in plane, cylindrical, and spherical standing wave fields", J. Acoust. Soc. Am., 1985, 77, 928-945.

Bauerecker, et al., "Formation and growth of ice particles in stationary ultrasonic fields", J. of Chem. Phys., 1998, 3709-3712.

Bazou, et al., "Physical Environment of 2-D Animal Cell Aggregates Formed in a Short Pathlength Ultrasound Standing Wave Trap", Ultrasound in Med. & Biol., 2005, 31, 423-430.

Benes, et al., "Abscheidung Dispergierter Teilchen Durch Ultraschall-Induzierte Koagulation", Taauna der Deutschen Arbeitsaameinschaft fur Akustik—DAGA '89, 1989, 1-4.

Benes, et al., "Improved quartz crystal microbalance technique", J. Appl. Phys., 1984, 56, 608-626.

Beverloo, et al., "Inorganic Phsophors as New Luminescent Labels for Irnmunocytochernistry and Time-Resolved Microscopy", Cytometry, 1990, 11, 784-792.

Bienvenue, et al., "Microchip-Based Cell Lysis and DNA Extraction from Sperm Cells for Application to Forensic Analysis", J. Forensic Sci., 2006, 51, 266-273.

Binks, et al., "Modern Aspects of Emulsion Science", The Royal Society of Chemistry, 1998, 310-321.

Bishop, et al., "Mechanism of higher brightness of PerCP-Cy5.5", Cytometry Supp, 2000, 10, 162-163.

Borisov, et al., "Blue LED Excitable Temperature Sensors Based on a New Eurpium (III) Chelate," J. Fluoresc., 2008, 18,581-589.

Borthwick, et al., "Development of a novel compact sonicator for cell disruption", J. of Microbioloaical Methods, 2005, 60, 207-216.

Bosma, et al., "Ultrasound, a new separation technique to harvest microlalgae", J. Appl. Phycology, 2003, 15, 143-153.

Bossuyt, et al., "Comparative Analysis for Whole Blood Lysis Methods for Flow Cytometry", Cytometry, 1997, 30, 124-133.

Brodeur, "Acoustic Separation in a Laminar Flow," Ultrasonics Symposium, 1994, pp. 1359-1362.

Caperan, et al., "Acoustic Agglomeration of a Glycol Fog Aerosol: Influence of Particle Concentration and Intensity of the Sound Field at Two Frequencies", J. Aerosol Sci., 1995, 26, 595-612.

Chase, et al., "Resolution of Dimly Fluorescent Particles: A Practical Measure of Fluorescence Sensitivity", Cytometry, 1998, 33, 267-279.

Coakley, et al., "Analytical scale ultrasonic standing wave manipulation of cells and microparticles", Ultrasonics, 2000, 38, 638-641.

Coakley, et al., "Cell-cell contact and membrane spreading in an ultrasound trap", Colloids and Surfaces B: Biointerfaces, 2004, 34, 221-230.

Coakley, et al., "Ultrasonic separations in analytical biotechnology", Tibtech, 1997, 15, 506-511.

Condrau, et al., "Time-Resolved Flow Cytometry for the Measurement of Lanthanide Chelate Fluorescence: I. Concept and Theoretical Evaluation", Cytometry, 1994, 16, 187-194.

Condrau, et al., "Time-Resolved Flow Cytometry for the Measurement of Lanthanide Chelate Fluorescence: II. Instrument Design and Experimental Results", Cytometry, 1994, 16, 195-205.

Cousins, et al., "Plasma Preparation from Whole Blood Using Ultrasound", Ultrasound in Med. & Biol., 2000, 26, 881-888.

Curtis, et al., "Ultrasonic Continuous Flow Plasmapheresis Separator", IBM Tech. Disc. Bulletin, 1982, 25,192-193.

Czyz, et al., "On the Concentration of Aerosol Particles by Means of Drift Forces in a Standing Wave Field", Acustica, 1990, 70, 23-28.

Dain, et al., "Dynamics of Suspended Particles in a Two-Dimensional High-Frequency Sonic Field", J. Aerosol Sci., 1995, 26, 575-594.

Dain, et al., "Side drift of aerosols in two-dimensional resonant acoustic levitators", J. Acoust. Soc. Am, 1997, 102, 2549-2555.

Danilov, et al., "Mean force on a small sphere in a sound field in a viscous fluid", J. Acoust. Soc. Am., 2000, 107, 143-153.

Danilov, et al., "The Mean Force Acting on a Small Body in an Axisymmetric Sound Field in a Real Medium", Izvestiva Adademii Nauk SSSR, Mekhanika Zhidkosti I Gaza, 1985, 5, 812-820.

Dean, et al., "Hydrodynamic Orientation of Sperm Heads for Flow Cytometry", Biophys. J., 1978, 23, 7-13.

Doblhoff-Dier, et al., "A Novel Ultrasonic Resonance Field Device for the Retention of Animal Cells", Biotechnol. Prog., 1994, 10, 428-432.

Doinikov, et al., "Acoustic radiation force on a spherical particle in a viscous heat-conducting fluid. I. General formula", J. Acoust. Soc. Am., 1997, 101, 713-721.

Doinikov, et al., "Acoustic radiation force on a spherical particle in a viscous heat-conducting fluid. II. Force on a rigid sphere", J. Acoust. Soc. Am., 1997, 101, 722-730.

Doinikov, et al., "Acoustic radiation force on a spherical particle in a viscous heat-conducting fluid. III. Force on a liquid drop", J. Acoust. Soc. Am., 1997, 101, 731-740.

Doinikov, et al., "Acoustic radiation pressure on a rigid sphere in a viscous fluid", Proc. R. Soc. Lond., 1994, 447-466.

Donnert, et al., "Major signal increase in fluorescence microscopy through dark-state relaxation", Nature Methods, 2007, 4, 81-86.

Doornbos, et al., "Experimental and Model Investigations of Bleaching and Saturation of Fluorescence in Flow Cytometry", Cytometry, 1997, 29,204-214.

EPO Application No. EP 08733084.1: Extended European Search Report dated Mar. 24, 2010.

Fenniri, et al., "Classification of Spectroscopically Encoded Resins by Raman Mapping and Infrared Hyperspectral Imaging", Journal of Combinatorial Chemistry, 2006, 8, 192-198.

Fulwyler, et al., "Hydronamic Orientation of Cells", Histochem. Cytoche., 1977, 7, 781-783.

Gaida, et al., "Selective Retention of Viable Cells in Ultrasonic Resonance Field Devices", Biotech. Prog., 1996, 12, 73-76.

Gao, et al., "Quantum Dot-Encoded Mesoporous Beads with High Brightness and Uniformity: Rapid Readout Using Flow Cytometry", Anal. Chem., 2004, 3, 2406-2410.

Gherardini, et al., "A New Immobilisation Method to Arrange Particles in a Gel Matrix by Ultrasound Standing Waves", Ultrasound in Med. & Biol., 1005, 31, 261-272, 2005.

Goddard, et al., "Single Particle High Resolution Spectral Analysis Flow Cytometry", Cytometry, 2006, 69A, 842-851.

Goddard, et al., "Ultrasonic particle concentration in a line-driven cylindrical tube", J. Acoust. Soc. Am., 2005, 117, 3440-3447.

Goddard, et al., "Ultrasonic Particle-Concentration for Sheathless Focusing of Particles for Analysis in a Flow Cytometer", Cytometry, 2006, 69, 66-74.

Goddard, et al., "Ultrasonic Concentration in a Line Driven Cylindrical Tube", Dissertation, 2004, 1-276.

Gonzalez, et al., "Precise Measurements of Particle Entertainment in a Standing-Wave Acoustic Field Between 20 and 3500 Hz", J. Aerosol Sci., 2000, 31,1461-1468.

Gor'Kov, et al., "On the forces acting on a small particle in an acoustical field in an ideal fluid", Soviet Physics-Doklady, 1962, 6, 773-775.

Gould, et al., "The effects of acoustic forces on small aprticles in suspension", Proceedings of the 1973 Symposium on Finite Amplitude Wave Effects in Fluids, Bjorno, L., ed., Pergamon, Guildford, 1974, 252-257.

Gould, et al., "Upper sound pressure limits on particle concentration in fields of ultrasonic standing-wave at megahertz frequencies", Ultrasonics, 1992, 30, 239-244.

Groschl, et al., "Automatische Frequenzregelung fur Piezoelektrische Resonatoren und deren Implementierung in akustischen Driftwellenresonator", Diplomarbeit Institut fur Allaemeine Phvsik, Technishchen Universitat Wien, 1991, 1-132.

Grossner, et al., "Single fiber model of particle retention in an acoustically driven porous mesh", Ultrasonics, 2003, 41, 65-74.

Grossner, et al., "Single-Collector Experiments and Modeling of Acoustically Aided Mesh Filtration", Amer. Inst. of Chem. Eng., 2005, 51, 1590-1598.

Grossner, et al., "Transport analysis and model for the performace of an ultrasonically enhanced filtration process", Chem. Ena. Sci., 2005, 60, 3233-3238.

Gupta, et al., "Acoustically driven collection of suspended particles within porous media", Ultrasonics, 1997, 35, 131-139.

Gupta, et al., "Fractionation of Mixed Particulate Solids According to Compressibility Using Ultrasonic Standing Wave Fields", Chem. Eng. Sci., 1995, 50, 3275-3284.

Haake, et al., "Contactless micromanipulation of small particles by an ultrasound field excited by a vibrating body", J. Acoust. Soc. Am., 2005, 117, 2752-2760.

Haake, et al., "Manipulation of Cells Using an Ultrasonic Pressure Field", Ultrasound in Med. & Biol., 2005, 31, 857-864.

Haake, et al., "Positioning of small particles by an ultrasound field excited by surface waves", Ultrasonics, 2004, 42, 75-80.

Habbersett, et al., "An Analytical System Based on a Compact Flow Cytometer for DNA Fragment Sizing and Single Molecule Detection", Cytometry 2004, 60A, 125-134.

Hager, et al., "A Summary of All Forces Acting on Spherical Particles in a Sound Field", Proc. of the Ultrasonic International '91 Conference and Exhibition, Le Touauet, France, 1991, 1-4.

Hamilton, et al., "Acoustic streaming generated by standing waves in two-dimensional channels of arbitrary width", J. Acoust. Soc. Am., 2003, 113, 153-160.

Hamilton, et al., "Linear and nonlinear frequency shifts in acoustical resonators with varying cross sections", J. Acoust. Soc. Am., 2001, 110, 109-119.

Hancock, "Observation of Forces on Microparticles in Acoustic Standing Waves", Thesis, submitted in partial satisfaction of the reaquirements for the degree of Master of Science in Biomedical Engineering, University of California, Davis, 2001, 1-155.

Harma, et al., "Zeptomole detection sensitivity of prostate-specific antigen in a rapid microtitre plate assay using time-resolved fluorescence", Luminescence, 2000, 15, 351-355.

Harris, et al., "A silicon microfluidic ultrasonic separator", Sensors and Actuators, 2004, 95, 425-434.

Harrison, et al., "Near-Infrared Photo- and Electroluminescence of Alkoxy-Substituted Poly (p-phenylene) and Nonconjugated Polymer/Lanthanide Tetraphenylporphyrin Blends", Chemistry of Materials, 2004, 16, 2938-2947.

Hatanaka, et al., "Effect of Process Parameters on Ultrasonic Separation of Dispersed Particles in Liquid", Jpn. J. ADPI. Phvs., 1999, 38, 3096-3100.

Hawkes, et al., "Continuous Cell Washing and Mixing Driven by an Unltrsound Standing Wave Within a Microfluidic Channel," Lab Chip, 4, (no month available) 2004, pp. 446-452.

Hawkes, J.J. et al., "A laminar flow expansion chamber facilitating downstream manipulation of particles concentrated using an ultrasonic standing wave", Ultrasonics, 1998, 36, 901-903.

Hawkes, J.J. et al., "Force field particle filter, combinin ultrasound standing waves and laminar flow", Sensors and Actuators B, 2001, 75, 213-222.

Hawkes, J.J. et al., "Microparticle manipulation in millimetre scale ultrasonic standind wave chambers", Ultrasonics, 1998, 36, 925-931.

Hawkes, J.J. et al., "Single half-wavelength ultrasonic particle filter: Predictions of the transfer matrix multilayer resonator model and experimental filtration results", J. Acoust. Soc. Am., 2002, 111, 1259-1266.

Hawkes, J.J. et al., "Ultrasonic deposition of cells on a surface", Biosensors and Bioelectronics, 2004, 19, 1021-1028.

Hemmila, I. et al., "Progress in Lanthanides as Luminescent Probes", J. Fluoresncence, 2005, 15, 529-542.

Hertz, H.M. et al., "Standing-wave acoustic trap for nonintrusive positioning of microparticles", J. Appl. Phys., 1995, 78, 4845-4849.

Higashitani, K.O. et al., "Migration of Suspended Particles in Plane Stationary Ultrasonic Field", Chem. Eng. Sci., 1981, 36, 1187-1192.

Hill M. et al., "Modelling in the design of a flow-through ultrasonic separator", Ultrasonics, 2000, 38, 662-665.

Hill M. et al., "Modelling of layered resonators for ultrasonic separation", Ultrasonics, 2002, 40, 385-392.

Hill, D.H. et al., "Operating Characteristics of Acoustically Driven Filtration Processes for Particulate Suspensions", Sep. Sci. and Tech., 2000, 35, 1363-1375.

Hill, M. et al., "The selection of layer thicknesses to control acoustic radiation forces profiles in layered resonators", J. Acoust. Soc. Am., 2003, 114(5), 2654-2661.

Hirschfeld, T. et al., "Fluorescence Background Discrimination by Prebleaching", J. Histochem. and Cytochem., 1979, 27, 96-101.

Holmes, D. et al., "High throughput particle analysis: Combining dielectrophoretic particle focussing with confocal optical detection", Biosensors and Bioelectronics, 2006, 21, 1621-1630.

Holwill, I.L. et al., "The use of ultrasonic standing waves to enhance optical particle sizing equipment", Ultrasonics, 2000, 38, 650-653.

Huhtinen, P. et al., "Synthesis, Characterization, and Application of Eu(III), Tb(III), Sm (III), and Dy(III) Lanthanide Chelate Nanoparticle Labels", Anal. Chem., 2005, 77, 2643-2648.

International Application No. PCT/US05/26524: International Search Report dated Oct. 3, 2006.

International Application No. PCT/US08/87579: International Search Report dated Feb. 9, 2009.

International Application No. PCT/US2008/059181: International Search Report dated Jul. 25, 2008.

International Application No. PCT/US2009/031154: International Search Report dated Jul. 8, 2009.

Invitrogen, "Fluo-4 NW Calcium Assay Kits (F36205, F36206)", Product Information, 2006.

Invitrogen, "Fluorophore selection guide for flow cytometry", Cellular Analvsis, 2007.

Johnston, P.A. et al., "Cellular platforms for HTS: three case studies", DDT, 2002, 7, 353-363.

Jonsson, H. et al., "Particle separation using ultrasound can be used with human shed mediastinal blodd", Perfusion, 2005, 20, 39-43.

Juarez, J.A. et al., "Piezoelectric Transducer for Air-Borne Ultrasound", Acustica, 1973, 29, 234-239.

Kaduchak, G. et al., "E6 diffraction catastrophe of the primary rainbow of oblate water drops: observations with white-light and laser illumination", Applied Optics, 1994, 33, 4691-4696.

Kaduchak, G. et al., "Hyperbolic umbilic and E6 diffraction catastrophes associated with the secondary rainbow of oblate water drops: observations with laser illumination", Applied Optics, 1994, 33, 4697-4701.

Kapishnikov, S. et al., "Continuous particle size separation and size sorting using ultrasound in a microchannel", J. Stat. Mech., 2006, 1-13.

Karumanchi, R.S. et al., "Field-assisted extraction of cells, particles and macromolecules", TRENDS is Biotech, 2002, 20, 72-78.

Kaye, P.H. et al., "Spatial light-scattering analysis as a means of characterizing and classifying non-spherical particles", Meas. Sci. Technol., 1998, 9, 141-149.

Kilburn, D.G. et al., "Enhanced Sedimentation of Mammalian Cells following Acoustic Aggregation", Biotech. and Bioeng., 1989, 34, 559-562.

King, L.V. et al., "On the acoustic radiation on spheres", Proc. R. Soc. A., 1933, 147, 212-240.

Kogan, S. et al., "Acoustic concentration of particles in piezoelectric tubes: Theoretical modeling of the effect of cavity shape and symmetry breaking", J. Acoust. Soc. Am., 2004, 116, 1967-1974.

Kozuka, T. et al., "Acoustic Micromanipulation Using a Multi-Electrode Transducer", 7th Inter. Svmp. on Micro Machine and Human Science IEEE, 1996, 163-170.

Kozuka, T. et al., "Control of a Standing Wave Field Using a Line-Focused Transducer for Two-Dimensional Manipulation of Particles", Jpn. J. Appl. Phys., 1998, 37, 2974-2978.

Kozuka, T. et al., "Micromanipulation Using a Focused Ultrasonic Standing Wave Field", Electronics and Communications in Japan, 2000, 83, 1654-1659.

Kumar, M. et al., "Fractionation of Cell Mixtures Using Acoustic and Laminar Flow Fields", Biotech. Bioeng., 2005, 89, 129-137.

Kundt, A. et al., "Longitudinal vibrations and acoustic figures in cylindrical columns of liquids", Annalen der Physik and Chemie (Poggendorff's Annalen), 1874, 153, 1-12.

Kuznetsove, L.A. et al., "Cavitation buble-driven cell and particle behavior in a ultrasound standing wave", J. Acoust. Soc. Am., 2005, 117, 104-112.

Kuznetsove, L.A. et al., "Microparticle concentration in short path length ultrasonic resonators: Roles of radiation pressure and acoustic streaming", J. Acoust. Soc. Am., 2004, 116, 1956-1966.

Kwiatkowski, C.S. et al., "Resonator frequency shift due to ultrasonically induced microparticle migration in an aqueous suspension: Observations and model for the maximum frequency shift", J. Acoust. Soc. Am., 1998, 103, 3290-3300.

Lakowicz, J.R. et al., "On the Possibility of Long-Wavelength Long-Lifetime High-Quantum-Yield Luminophores", Analyical Biochemistry, 2001, 288, 62-75.

Leif, R.C. et al., "Increasing the Luminescence of Lanthanide Complexes", Cytometry, 2006, 69A, 767-778.

Leif, R.C. et al., "Markers for Instrumental Evaluation of Cells of the Female Reproductive Tract; Existing and New Markers", in The Automation of Uterine Cancer Cytology Tutorials of Cytology, (edited by G.L. Wied. et al.), 1976, 313-344.

Lierke, E.G. et al., "Acoustic Positioning for Space Processing of Materials Science Samples in Mirror Furnaces", IEEE Ultrasonics Symposium, 1983, 1129-1139.

Lilliehorn, T. et al., "Trapping of microparticles in the rear field of an ultrasonic transducer", Ultrasonics, 2005, 43, 293-303.

Lofstedt, R. et al., "Theory of long wavelength acoustic radiation pressure", J. Acoust. Soc. Am., 1991, 90, 2027-2033.

Loken, M.R. et al., "Cell Discrimination by Multiangle Light Scattering", Histochem. Cytochem., 1976, 24, 284-291.

Loken, M.R. et al., "Identification of Cell Asymmetry and Orientation by Light Scattering", Histochem. Cytochem., 1977, 7, 790-795.

Macey, M.G. et al., "Comparative Study of Five Commercial Reagents for Preparing Normal and Leikaemic Lymphoctyes for Immunophenotypic Analysis by Flow Cytometry", Cytometry, 1999, 38, 153-160.

Maltsev, V.P. et al., "Scanning flow cytometry for individual particle analysis", Review of Scientific Instruments, 2000, 71, 243-255.

Mandralis, Z. et al., "Enhanced synchronized ultrasonic and flow-field fractionation of suspensions", Ultrasonics, 1994, 32, 113-121.

Mandralis, Z. et al., "Transient Response of Fine Particle Suspensions to Mild Planar Ultrasonic Fields", Fluid/Particle Separation J., 1990, 115-121.

Marston, P.L. et al., "Generalized rainbows and unfolded glories of oblate drops: organization for multiple internal reflection and extension of cusps into Alexander's dark band", Applied Optics, 1994, 33, 4702-4713.

Marston, P.L. et al., "Manipulation of Fluid Objects with Acoustic Radiation Pressure", Ann. N.Y. Acad. Sci., 2004, 1027, 414-434.

Marston, P.L. et al., "Resonances, Radiation Pressure, and Optical Scattering Phenomena of Drops and Bubbles", Proceedings of the Second International Colloquium on Drops and Bubbles, Jet Prop. Lab. Pub 82-7 Pasadena, CA, 1982, 166-174.

Marston, P.L., "Tensile Strength and Visible Ultrasonic Cavitation of Superfluid 4He*," Journal of Low Temperature Physics, 25(3/4), Mar. 5, 1976, pp. 383-407.

Martin, K.M. et al., "Acoustic filtration and sedimentation of soot particles", Experiments in Fluids, 1997, 23, 483-488.

Masudo, T. et al., "Particle Characterization and Separation by a Coupled Acoustic-Gravity Field", Analytical Chemistry 2001, 73, 3467-3471.

Mathies, R.A. et al., "Optimization of High-Sensitivity Fluorescence Detection", Anal. Chem., 1990, 62, 1786-1791.

Mazumdar, M.K. et al., "Single particle aerodynamic relaxation time analyzer", Rev. Sci. Instrum., 1977, 48, 622-624.

Mazumdar, M.K. et al., "Spart Analyzer: Its Application to Aerodynamic Size Distribution Measurement", J. Aerosol Sci., 1979, 10, 561-569.

McCartin, B.J., "A Numerical Procedure for 2D Acoustic Waveguides with Heated Walls", http://flux.aps.org/meetings/YR99/OSS99/abs/S700004.html, 1999.

Meindersma, G.W. et al., "Separation of a biocatalyst with ultrafiltration or filtration after bioconversion", J. Membrane Sci., 1997, 125, 333-349.

Morgan, J. et al., "Manipulation of in vitro toxicant sensors in an ultrasonic standing wave", Toxicology in Vitro, 2004, 18, 115-120.

Mullaney, P.F, et al., "The Small Angle Light Scattering of Biological Cells", Biophys. J., 1970, 10, 764-772.

Neild, A. et al., "Design, modeling and characterization of microfluidic devices for ultrasonic manipulation", Sensors and Actuators B: Chemical , Feb. 20, 2007, 121(2).

Neukammer, J. et al., "Angular distribution of light scattered by single biological cells and oriented particle agglomerates", Appl. Opt., 2003, 42, 6388-6397.

Nilsson, A. et al., "Acoustic control of suspended particles in micro fluidic chips", Lab Chip, 2004, 4, 131-135.

Nolan et al., "Suspension Array Technology: New Tools fro Gene and Protein Analysis", Cell and Molecular Biology, 2001, 47, 1241-1256.

Nowotny, H. et al., "Layered piezoelectric resonators with an arbitrary number electrodes (general one-dimensional treatment)", J. Acoust. Soc. Am., 1991, 90, 1238-1245.

Otaki, M. et al., "Virus Removal in a Membrane Separation Process", Water Sci. and Tech., 1998 37, 107-116.

Pangu, G.D. et al., "Acoustically aided separation of oil droplets from aqueous emulsions", Chem. Eng. Sci., 2004, 59, 3183-3193.

Petersson, F. et al., "Carrier Medium Exchange through Ultrasonic Particle Switching in Microfluidic Channels", Anal. Chem., 2005, 77, 1216-1221.

Petersson, F. et al., "Continuous separation of lipid particles from erythrocytes by means of laminar flow and acoustic standing wave forces", Lab Chip, 2005, 5, 20-22.

Petersson, F. et al., "Free Flow Acoustophoresis: Microfluidic-Based Mode of Particle and Cell Separation", Anal. Chem., 2007 79, 5117-5123.

Petersson, F., "Particle Flow Switch Utilizing Ultrasonic Particle Switching in Microfluidic Channels", 7th International Conf on Miniaturizing Chem and Biochem Analysis Systems, 2003, 879-882.

Pregibon, D.C. et al., "Multifunctional Encoded Particles for High-Throughput Biomolecule Analysis", Science, 2007, 315, 1393-1396.

Princen, K. et al., "Evaluation of SDF-1/CXCR4-Induced Ca2+Signaling by Fluorometric Imaging Plate Reader (FLIPR) and Flow Cytometry", Cytometry, 2003, 51A, 35-45.

Pui, P.W. et al., "Batch and Semicontinuous Aggregattion and Sedimentation of Hybridoma Cells by Acoustic Resonance Fields", Biotechnol. Prog., 1995, 11, 146-152.

Rama Rao, G.V. et al., "Monodisperse Mesoporous Silica Microspheres Formed by Evaporation-Induced Self Assembly of Surfacant Templates in Aerosols", Advanced Materials, 2002, 18, 1301-1304.

Rens, W. et al., "A Novel Nouel for More Efficient Sperm Orientation to Improve Sorting Efficiency of X and Y Chromosome-Bearing Sperm", Cytometry, 1998, 33, 476-481.

Ricks, D.C. et al., "A numerically stable global matrix method for cylindrically layered shells excited by ring forces", J. Acoust. Soc. Am., 1994, 95, 3339-3349.

Rouleau, F. et al., "Electromagnetic scattering by compact clusters of spheres", Astron. Astrophys., 1996, 310, 686-698.

Rudnick, J. et al., "Oscillational instabilities in single-mode acoustic levitators", J. Acoust. Soc. Am., 1990, 87, 81-92.

Saito, M. et al., "Microorganism manipulation and microparticle arrangement by the use of ultrasonic standing waves", SPIE, 2001, 4590, 26-37.

Saito, M. et al., "Quantum mechanical representation of acoustic streaming and acoustic radiation pressure", Physical Review, 2001, E64, 026311-1-026311-5.

Saito, M. et al., "Ultrasonic manipulation of locomotive microorganisms and evaluation of their activity", J. App. Physics, 2002, 92, 7581-7586.

Saito, M. et al., "Ultrasonic trapping of paramecia and estimation of their locomotive force", Appl. Phys. Lett, 1997, 71, 1909-1911.

Saito, M. et al., "Ultrasonic waves for fabricating lattice structure in composite materials", SPIE, 1999, 3786, 179-190.

Samiotaki, M. et al., "Seven-Color Time-Resolved Fluorescence Hybridization Analysis of Human Papilloma Virus Types", Analytical Biochem., 1997, 253, 156-161.

Schmid, M. et al., "A computer-controlled system for the measurement of complete admittance spectra of piezoelectric resonators", Meas. Sci. Technol., 1990, 1, 970-975.

Schoell, W.M. et al., "Separation of Sperm and Vaginal Cells with Flow Cytometry for DNA Typing After Sexual Assault", Obstetrics and Gynecolony, 1999, 94, 623-627.

Semianov, K.A. et al., "Measurement of Mammalian Erythrocyte Indices from Light Scattering with Scaning Flow Cytometer", Proc. SPIE, 2003, 5141, 106-113.
Sethu, P. et al., "Continuous Flow Microfluidic Device for Rapid Erythrocyte Lysis", Anal. Chem., 2004, 76, 6247-6253.
Shapiro, H.M. et al., Practical Flow Cytometry, Hoboken, NJ, John Wiley & Sons. Inc., 2005, 9-13.
Shvalov, A.N. et al., "Individual *Escherichia coli* Cells Studied from Light Scattering with the Scanning Flow Cytometer", Cytometry, 2000, 41, 41-45.
Shvalov, A.N. et al., "Light-scattering properties of individual erythrocytes", Applied Optics, 1999, 38, 230-235.
Simpson, H.J. et al., "Ultrasonic four-wave mixing mediated by an aqueous suspension of microspheres: Theoretical steady-state properties", J. Acoust. Soc. Am., 1995, 98, 1731-1741.
Skudrzyk, E. et al., "Die Grundlagen der Akustik", Sprinaer Verlaa. Wien, 1954, 202-205 and 807-825.
Slomkowski, S. et al., "New Types of Microspheres and Microsphere-related Materials for Medical Diagnostics", Polymers for Advanced Technologies, 2002, 13, 906-918.
Sobanski, M.A. et al., "Sub-micron particle manipulation in an ultrasonic standing wave: Applications in detection of clinically important biomolecules", Bioseparation, 2001, 9, 351-357.
Steinkamp, J.A. et al., "Dual-Laser, Differential Fluorescence Correction Method for Reducing Cellular Background Autofluorescence", Cytometry, 1986, 7, 566-574.
Steinkamp, J.A. et al., "Enhanced Immunofluorescence Measurement Resolution of Surface Antigens on Highly Autofluorescent, Glutaraldehyde-Fixed Cells Analyzed by Phase-Sensitive Flow Cytometry", Cytometry, 1999, 37, 275-283.
Steinkamp, J.A., "A Differential Amplifier Circuit for Reducing Noise in Axial Light Loss Measurements", Cyometry, 1983, 4, 83-87.
Stewart, C.C. et al., "Resolving Leukocytes Using Axial Light Loss", Cytometry, 1989, 10, 426-432.
Stoffel, C.L. et al., "Data Analysis for a Dual Analysis for a Dual-Channel Virus Counter", Analytical Chemistry, 2005, 77, 2243-2246.
Stoffel, C.L. et al., "Design and Characterization of a Compact Dual Channel Virus Counter", Cytometry, 2005, Part A 65A, 140-147.
Stovel, R.T. et al., "A Means for Orienting Flat Cells in Flow Systems", Biophys J., 1978, 23, 1-5.
Takeuchi, J. et al., "Ultrasonic Micromanipulator Using Visual Feedback", Jpn J. Appl. Phys., 1996, 35, 3244-3247.
Takeuchi, M. et al., "Ultrasonic Micromanipulation of Small Particles in Liquid", Jpn J. Appl. Phys., 1994, 33, 3045-3047.
Thiessen, D.B. et al., "Principles of some Acoustical, Electrical, and Optical Manipulation Methods with Applications to Drops, Bubbles, and Capillary Bridges", ASME Fluids Eng. Div. Publ. FED, 1998.
Thiessen, D.B. et al., "Some Responses of Small Diffusion Flames to Ultrasonic Radiation", NASA, 2003, 321-324.
Tolt, T.L. et al., "Separation devices based on forced coincidence response of fluid-filled pipes", J. Acoust. Soc. Am., 1992, 91, 3152-3156.
Tolt, T.L. et al., "Separation of Dispersed Phases from Liquids in Acoustically Driven Chambers", Chem. Eng. Science, 1993, 48, 527-540.
Townsend, R.J. et al., "Modelling of particle paths passing through an ultrasonic standing wave", Ultrasonics, 2004, 42, 319-324.
Trihn, E.H. et al., "Experimental study of streaming flows associated with ultrasonic levitators", Phys. Fluids, 1994, 6, 3567-3579.
Trinh, E.H. et al., "Compact acoustic levitation device for studies in fluid dynamics and material science in the laboratory and microgravity", Rev. Sci. Instrum., 1985, 56, 2059-2065.
Tuckermann, R. et al., "Trapping of heavy gases in stationary ultrasonic fields", Chem. Phys. Ltrs., 2002, 363, 349-354.
Tung, Yi-C. et al., "PDMS-based opto-fluidic micro flow cytometer with two-color, multi-angle fluorescence detection capability using PIN photodiodes", Sensors and Actuators, 2004, 98, 356-367.
Tyson, D.S. et al., "Ruthenium (II) complex with a notably long excited state lifetime", The Royal Society of Chemistry, 2000, 2355-2356.
Vainshtein, P. et al., "On the Drift of Aerosol Particles in Sonic Fields", J. Aerosol Sci., 1992, 23, 631-637.
Vainshtein, P. et al., "The effect of centreline particle concentration in a wave tube", J. Fluid Mech., 1996, 306, 31-42.
Van Hee, P. et al., "Strategy for Selection of Methods for Separation of Bioparticles From Particle Mixtures", Biotech. Bioeng., 2006, 94, 689-709.
Verpoorte, E. et al., "Beads and chips: new recipes for analysis—Elisabeth Verpoorte reviews particle handling in microchannels", Lab Chip, 2003, 3, 60N-68N.
Visuri, S.V. et al., "Microfluidic tolls for biological sample preparation", Poster 1423, 2nd Annual International IEEE-EMBS Special Topic Cofnerence on Microtechnologies in Medicine & Biology, May 2-24, 2002 556-559.
Wang, Z. et al., "Retention and Viability Characteristics of Mammalian Cells in an Acoustically Driven Polymer Mesh", Biotechnol. Prog., 2004, 20, 384-387.
Ward, M. et al., "Manipulation of Immunomagnetic Targets in Microfluidic Channel Flow", Dissertation, 2005, 1-205.
Weiser, M.A. et al., "Interparticle Forces on Red Cells in a Standing Wave Field", Acustica, 1984, 56, 114-119.
Weiser, M.A.H. et al., "Extension of acoustic levitation to include the study of micron-size particles in a more compressible host liquid", J. Acoust. Soc. Am., 1982, 71, 1261-1268.
Whitworth, G. et al., "Particle column formation in a stationary ultrasonic field", J. Acoust. Soc. Am., 1992, 91, 79-85.
Whitworth, G. et al., "Transport and harvesting of suspended particles using modulated ultrasound", Ultrasonics, 1991, 29, 439-444.
Wu, Y. et al., "Diazo Coupling Method for Covalent Attachment of Proteins to Solid Substrates", Bioconjugate Chem., 2006, 17, 359-365.
Yagi, et al., "Flow Cytometry to Evaluate *Theileria sergenti* Parasitemia Using the Florescent Nucleic Acid Stain SYTO16," Cytometry, 41, (no month available) 2000, pp. 223-225.
Yamakoshi, Y. et al., "Micro particle trapping by opposite phases ultrasonic travelling waves", Ultrasonics, 1998, 36, 873-878.
Yasuda, K. et al., "Blood Concentration by Superposition of Higher Harmonics of Ultrasound", Jpn. J. Appl. Phys., 1997, 36, 3130-3135.
Yasuda, K. et al., "Concentration and Fractionation of Small Particles in Liquid by Ultrasound", Jpn J. Appl. Phys., 1995, 34, 2715-2720.
Yasuda, K. et al., "Deoxyribonucleic acid concentration using acoustic radiation force", J. Acoust. Soc. Am., 1996, 99, 1248-1251.
Yasuda, K. et al., "Non-destructive, non-contact handling method for biomaterials in micro-chamber by ultrasound", Sensors and Actuators, 2000, 64, 128-135.
Yasuda, K. et al., "Particle separation using acoustic radiation force and elecrostatic force", J. Acoust. Soc. Am., 1996, 99, 1965-1970.
Yasuda, K. et al., "Using acousitc radiation force as a concentration method for erythrocytes", J. Acoust. Soc. Am., 1997, 102, 642-645.
Ye, C-H. et al., "Preparation of three terbium complexes with paminobenzoic acid and investigation of crystal structure influence on luminescence property", Journal of Solid State Chemistry, 2004, 177, 3735-3742.
Yosioka, K. et al., "Acoustic Radiation Pressure on a Comressible Sphere", Acustica, 1955, 5, 167-173.
Yuan, J. et al., "Lanthanide-based luminescence probes and time-resolved luminescence bioassays", Trends in Analytical Chernistry, 2006, 25, 490-500.
Yurkin, M.A. et al., "Experimental and theoretical study of light scattering by individual mature red blook cells by use of scanning flow cytometry and a discrete dipole approximation", Applied Optics, 2005, 44, 5249-5256.
Aleksandrov, et al., "Pulsed Laser Florescence Spectrometer," Zhurnal Prikladnoi Spektroskopii, Oct. 1987, 47(4), 686-692.
Borgnis, "Acoustic Radiation Pressure of Plane Compressional Waves," *Reviews of Modern Physics*, Jul. 1953, 25(3), 653-664.
Cheung, et al., "Impedance Spectroscopy Flow Cytometry: On-Chip Label-Free Cell Differentiation," *Cytometry Part A*, Feb. 10, 2005, 65A, 124-132.
Haake, et al., "Positioning, Displacement, and Localization of Cells Using Ultrasonic Forces," Biotechnology and Bioengineering, 92(1), Aug. 10, 2005, 8-14.

Keij, et al., "Coincidence in High-Speed Flow Cytometry: Models and Measurements," Cytometry 12, Jan. 22, 1991, 398-404.

Petersson et al., "Separation of Lipids from Blood Utilizing Ultrasonic Standing Waves in Microfluidic Channels," *Analyst*, 2004, 129, 938-943.

Response to Mar. 24, 2010 Extended European Search Report in European Application No. 08733084.1 filed Jun. 16, 2010.

International Application No. PCT/US08/87579, Written Opinion dated Feb. 9, 2009.

U.S. Appl. No. 11/923,403: Non-Final Office Action dated Sep. 3, 2008.

U.S. Appl. No. 11/923,403: Final Office Action dated Jan. 14, 2009.

* cited by examiner

METHOD FOR NON-CONTACT PARTICLE MANIPULATION AND CONTROL OF PARTICLE SPACING ALONG AN AXIS

CROSS REFERENCE TO RELATED APPLICATION

This application is a continuation-in-part of U.S. patent application Ser. No. 11/923,403, filed Oct. 24, 2007.

STATEMENT REGARDING FEDERAL RIGHTS

This invention was made with government support under Contract No. DE-AC52-06NA25396 awarded by the U.S. Department of Energy. The government has certain rights in the invention.

FIELD OF THE INVENTION

The present invention relates to a method for manipulating particles and controlling spacing thereof along an axis in a flowing liquid.

BACKGROUND OF INVENTION

Piezoelectric droplet generation devices used for inkjets have been adapted for use with coulter volume and optical sensing to perform the first sorting of biological cells. The basics of this system have remained mostly unchanged since then. A hydrodynamically focused sample stream containing particles is optically interrogated (for scatter or fluorescence) either just prior or just after the focused stream is ejected into the air. The ejected stream is vibrated through the use of piezoelectric transducers, which generate waves within the sample stream leading to droplet formation. This process can lead to very regularly and predictably spaced droplets which can then be charged and deflected to be either kept for further analysis or discarded. This is one common format generally referred to as flow cytometry or often as fluorescence activated cell sorting (FACS).1

However, several factors limit the speed at which this process can take place. The maximum drop formation rate requires nearly 3.45 MPa to drive $2.5 \times 10^5$ drops per second, though practically, mechanical limitations of the flow cytometer as well as effects on cells restrict the pressure applied to the system, limiting the rate to $1.0 \times 10^5$ drops per second. Additionally, because the particle arrival rate is stochastic, the maximum sort rate is additionally limited to approximately $2.5 \times 10^4$ particles per second. Further, the uncertain position of the particles in the flow stream leads to empty droplets, droplets with multiple particles, and particles at the break-off point between one droplet and another, all of which can lead to aborted sorting events, and all of which greatly reduce the overall sort rate.

Particle sorters of this type have problems with large particles (particles of diameter greater than $1 \times 10^4$ meters) such as multicellular organisms, multicellular spheroids, and large microspheres typically used for combinatorial library synthesis. Large particle sorters generally needed larger flow channels and exit orifices to prevent the randomly arriving particles from clogging and to prevent particle effects on droplet break-offs. However, these larger flow channels restricted the linear velocity of the flow stream due to problems caused by increased turbulence. Also, as particles took up an increasing proportion of the exit orifice, droplet formation was disturbed, effectively limiting the size of particles to about 20% the size of the exit orifice or less. Combined, these factors restricted the sorting rate of large particles to roughly 1000 per second. Some work has been done with acoustic focusing of particles, though this has not corrected the problem of random particle arrival.

Some alternative methods have been attempted, such as a high pressure air jet that deflects the flow stream unless an analysis indicates that the particles in the stream should be kept at which point the air jet shuts down allowing the particles to pass through (though this method is limited to only about 15-1000 particles per second), a fluidic switching approach which is typically mechanical in nature (limited to only about 500 particles per second), and a laser ablation approach (though this method is no faster than current techniques leaves significant cell debris and is not suitable for sorting of microspheres).

Consequently, a need has long been felt for a method of assuring predictable arrival of particles to ensure accurate high speed sorting of large particles in a flowing system.

SUMMARY OF THE INVENTION

The present invention meets the aforementioned need by generating acoustic, non-sinusoidal wave forms along the central axis of a flowing system (i.e., parallel with the flow). Whereas positioning particles in a liquid using standing or travelling waves is known, prior systems have utilized a standing wave in a closed (non-flowing) system where there are walls or barriers to reflect the wave and maintain a standing waveform. The challenge has been to acoustically focus particles in a flowing system such that the particles remain singularly and uniformly spaced along the central axis of an open (e.g., flowing) system. The particles are able to exit the flowing system individually and consistently, meaning that there are few if any gaps in particles exiting the system, which results in "lost" analysis time. In one embodiment, the particles are subjected to dielectrophoresis, which allows one to vary the distance between the uniformly spaced particles.

The following provide some non-limiting embodiments of the present invention.

According to one embodiment, a method of uniformly spacing particles in an open, flowing system is provided, comprising suspending particles in an elongated fluid filled cavity; exposing said cavity to an axial acoustic standing wave field, wherein said axial acoustic standing wave field drives said particles to nodal and anti-nodal positions along the center axis of said cavity to result in uniformly spaced particles; and focusing said particles to the center axis of said cavity.

According to another embodiment of the present invention, a system for uniformly spacing particles in an open, flowing system comprising an elongated cavity filled with a flowing fluid and further comprising suspended particles; and a transducer acoustically and communicably linked to said cavity wherein said transducer vibrates to create an axial acoustic standing wave field, and wherein said axial acoustic standing wave field results in substantially uniformly spaced nodes along the flow axis of said cavity; and wherein said axial acoustic standing wave field drives a single particle to a substantially uniformly spaced node along the center axis of said cavity.

BRIEF DESCRIPTION OF THE DRAWINGS

For a better understanding of the present invention, reference may be made to the accompanying drawings in which.

DETAILED DESCRIPTION OF THE INVENTION

The present invention provides for a method of non-contact particle manipulation and control of particle spacing along an axis by means of axial acoustic standing wave fields and a means for radially focusing said particles along the central axis. Particles are suspended in an aqueous solution, and this solution then flows into the cylindrical flow channel.

A transducer is used to create an axial acoustic standing wave field in the flow channel parallel to the axis of the flow channel. This drives a particle to a node or an anti-node of the axial standing wave at half-wavelength intervals, depending on whether the particles are more or less dense and more or less compressible than the surrounding fluid. Once the particles have been focused and driven to half-wavelength positions along the center axis of the flow channel and positioned to the center of the channel, for example by using hydrodynamic, acoustic or other means, the flow stream exits the flow channel, with particles uniformly spaced. This allows for synchronization of droplet formation and particle arrival, such that a droplet is not created until a particle is present, or such that droplets always contain a particle. Embodiments of the present invention may be combined with recent low cost flow cytometry developments in lasers (such as a self healing laser beam, a single laser focused to a line, multiple laser beams, and diode pumped solid-state lasers) and data acquisition systems (such as multianode photomultiplier tubes, fiber optics, avalanche photodiodes, low cost digital signal processing chips with onboard analogue-to-digital converters, and charge couple device technology), to create inexpensive low linear velocity parallel flow cytometry analyzers to maximize particle throughput. These embodiments of the present invention and assorted methods and devices can be combined with periodic droplet creation and new droplet-on-demand particle sorters (using focused piezo methods and flexural piezo methods) that are less limited by particle size to form less expensive large particle sorters.

Herein, "uniformly spaced" is understood to mean that the distance between each particle is substantially equal, and corresponds to the distance between two nodes or anti-nodes. In one embodiment, a single particle is associated with a single node or anti-node.

Herein, "open" is understood to mean a system suitable for containing a flowing liquid, for example a cylindrical shaped container, wherein at least one end contains no physical or air barrier to reflect an acoustic wave. In other words, fluid flows freely through at least one end of the system to, e.g., an analyzer.

Figure 1:
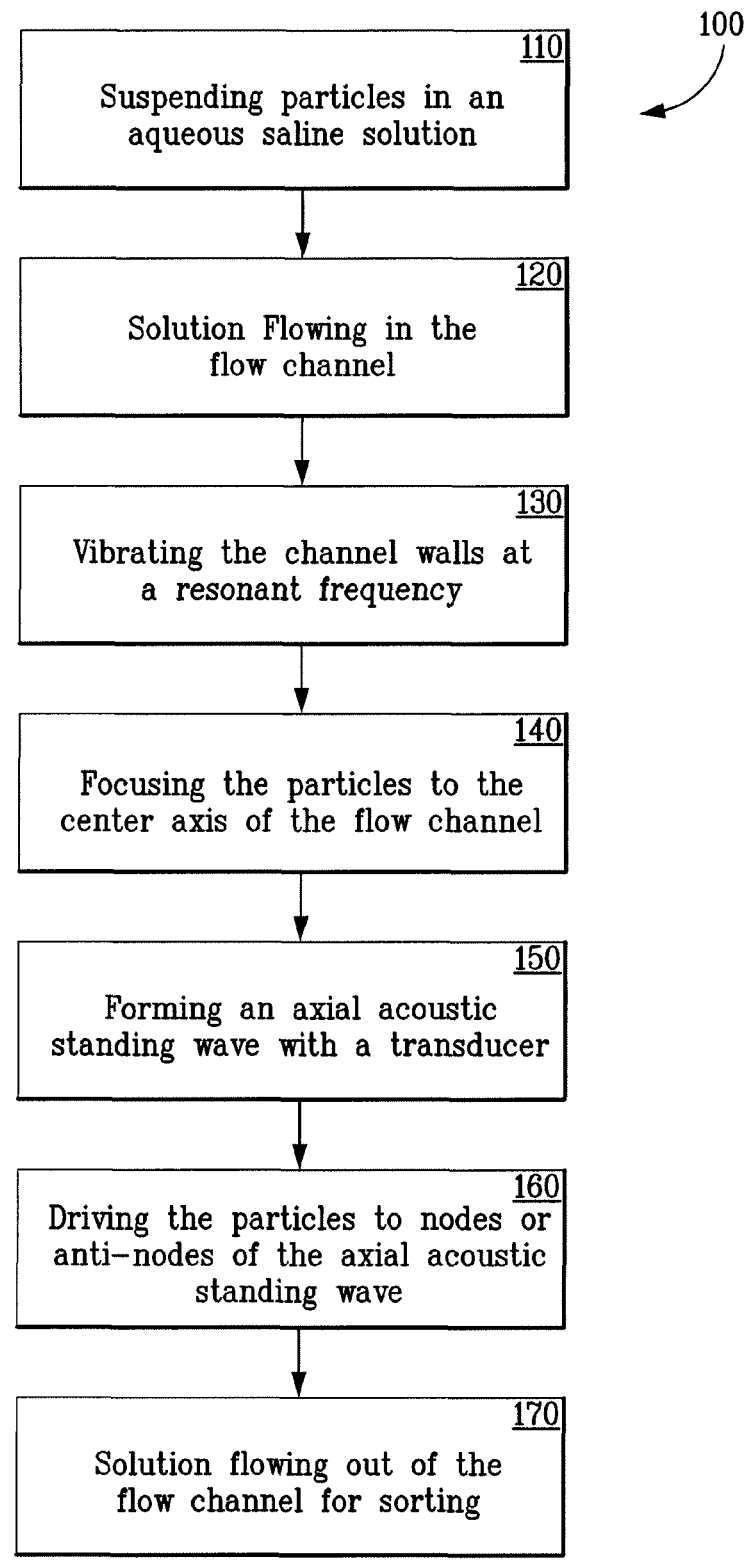
FIG. 1 illustrates a flow chart of the method for controllably spacing particles along an axis using two acoustic standing wave fields.

FIG. 1 illustrates a flow chart of a method for controllably spacing particles along an axis using acoustic standing wave fields 100 according to an embodiment of the present invention. The first step in the process of controlling the spacing between particles is suspending the particles in, for example, an aqueous saline solution 110. Next, the step of the solution flowing into the flow channel 120 occurs, where the step of vibrating the channel walls at a resonant frequency 130 takes place. The vibration of the chamber walls at a resonant frequency causes a radial acoustic standing wave field to form, which performs the next step of focusing the particles to the center axis of the flow channel 140. At the same time, the step of forming an axial acoustic standing wave with a transducer 150 occurs, where the axial acoustic standing wave is parallel to the center axis of the flow channel. This axial acoustic standing wave causes the step of driving the particles to nodes or anti-nodes of the axial acoustic standing wave 160 to happen. At this point, the particles are spaced at uniform half-wavelength intervals along the center axis of the flow channel, and the final step of the solution flowing out of the flow channel for sorting 170 ensues.

One embodiment of a flow channel can be a cylindrical quartz capillary tube with an inner diameter of about approximately 200 μm, and the vibration of the chamber walls is driven by an acoustic flow cell with piezoelectric sources in contact with the outside of the flow channel. This acoustic flow cell can be driven at a frequency of about 5 MHz. The transducer that forms the axial acoustic standing wave field can also be an acoustic flow cell with piezoelectric sources in contact with the outside of the flow channel. The particles are focused to a stream with a diameter of about approximately 10 μm.

In all embodiments, the solution could be something other than an aqueous saline solution. The flow channel may be a non-cylindrical shape, and may be made of a substance other than quartz, such as glass or plastic, and have a different diameter other than the 200 μm inner diameter discussed above, though not so large that the increasing diameter causes excessive turbulence. The acoustic standing wave fields may also be other than acoustic wave fields, such as magnetic field, electric fields, gravitational fields, and optical field. The frequency may be other than 5 MHz, but should be appropriately high to avoid cavitation—typically higher than 1 MHz. The focused stream of particles may also have a diameter of other than 10 μm depending on the size of the particles and the flow channel. Also, this method may be used in a parallel analysis situation, in which a plurality of flow channels run in parallel to accomplish the sorting in less time.

Figure 2:
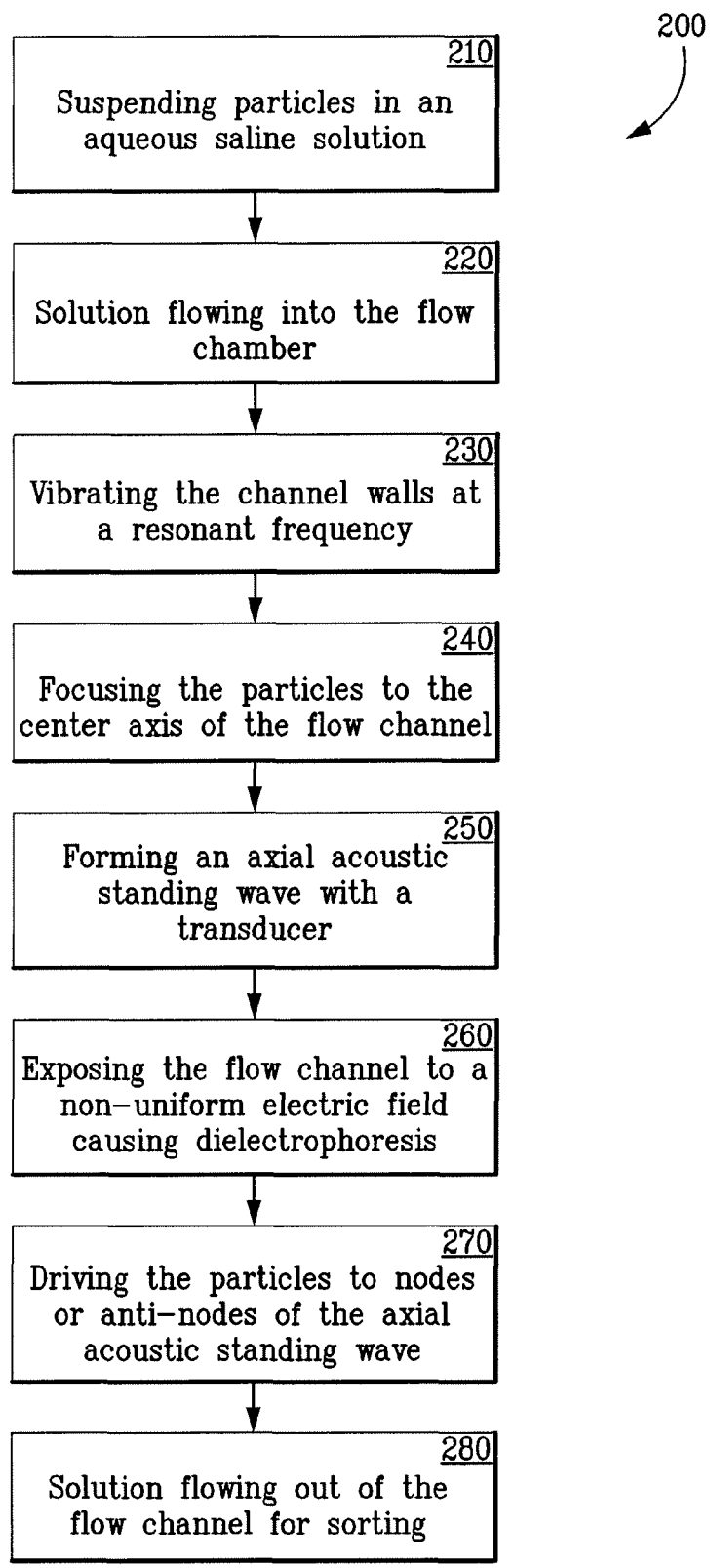
FIG. 2 illustrates a flow chart of the method for controllably spacing particles along an axis using two acoustic standing wave fields and a non-uniform electric field.

FIG. 2 illustrates a flow chart of a method for controllably spacing particles along an axis using acoustic standing wave fields and a non-uniform electric field 200, according to one embodiment of the present invention. The process can include the step of controlling the spacing between particles by suspending the particles in, for example, an aqueous saline solution 210. The process can also include the step of the solution flowing into the flow channel 220, where the step of vibrating the chamber walls at a resonant frequency 230 takes place. This vibration of the channel walls at a resonant frequency causes a radial acoustic standing wave field to form, which performs the step of focusing the particles to the center axis of the flow channel 240. The process can also include the step of forming an axial acoustic standing wave with a transducer 250, where the axial acoustic standing wave is parallel to the center axis of the flow channel. Simultaneously, the step of exposing the flow channel to a non-uniform electric field causing dielectrophoresis 260 occurs. The two steps of forming an axial acoustic standing wave with a transducer 250 and exposing the flow channel to a non-uniform electric field causing dielectrophoresis 260 cause the step of driving the particles to nodes or anti-nodes of the axial acoustic standing wave 270 to happen. These nodes and anti-nodes are more narrowly spaced than those occurring in FIG. 1, because the additional step of exposing the flow channel to a non-uniform electric field causing dielectrophoresis 270 allows for more precision in positioning the particles, and allows the axial standing waves to have a higher frequency and therefore a smaller wavelength. At this point, the particles are spaced at uniform half-wavelength intervals along the center axis of the flow channel, and the final step of the solution flowing out of the flow channel for sorting 280 ensues.

This combination system is constructed using a microfluidic channel design. It can have a planar structure with a lead zirconate titanate (PZT) mounting substrate as the generation mechanism for the ultrasonic manipulation field. A non-uniform electrode surface at the fluid/PZT interface creates the necessary field gradient for the dielectrophoresis, driven at the same frequency as the ultrasonic field. The frequency of acoustic excitation is sufficiently high so as to eliminate potential problems of electrolysis and deleterious transport by electrophoresis. Since the forces generated by the dielectrophoresis are relatively small, sorter electrodes typically have an elongated shape to maximize the time a particle experiences the sideward force and achieve the required displacement with a relatively low force. To improve the sorting speed, the sorter elements are elongated even more.

Figure 3:
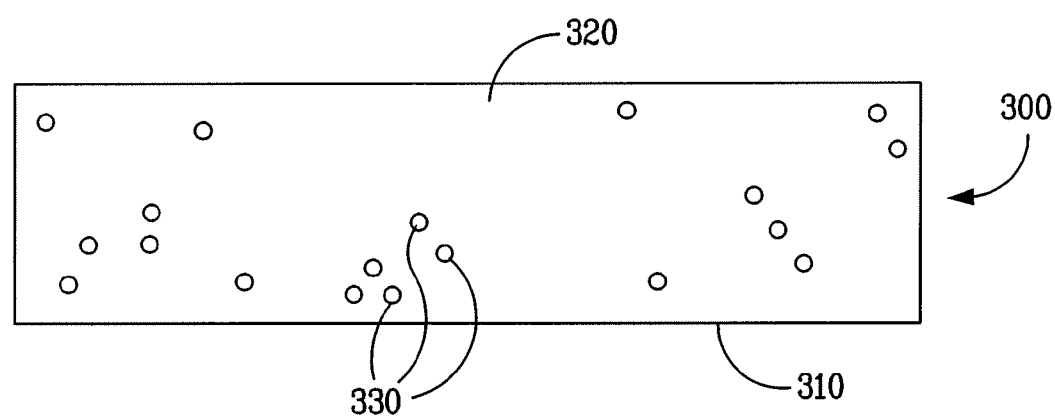
FIG. 3 illustrates a flow channel in which particles are spaced randomly.

FIG. 3 illustrates a prior art flow channel 300. The prior art flow channel 300 includes a quartz flow channel 310, an aqueous saline solution 320, and particles 330. The quartz flow channel 310 contains the aqueous saline solution 320, and the particles 330 are suspended in the aqueous saline solution 320.

In operation, the aqueous saline solution 320, in which the particles 330 are suspended, flows through the quartz flow channel 310. The particles 330, however, are randomly dispersed throughout the aqueous saline solution 320 because there are no outside forces acting upon this prior art flow channel 300 to position the particles 330 in any specific manner. Thus, the particles 330 flow into, through, and out of the quartz flow channel 310 without any uniformity as to where they are located within or the intervals at which they exit from the quartz flow channel 310.

Figure 4:
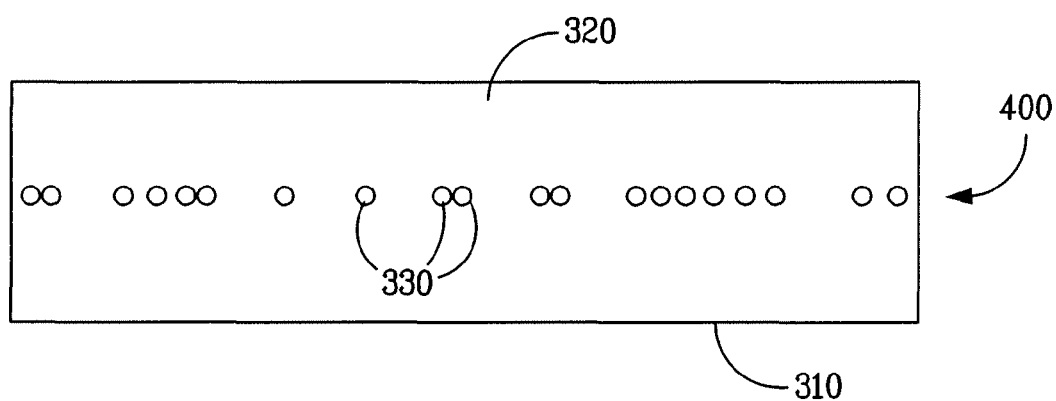
FIG. 4 illustrates a flow channel that has been exposed to a radial acoustic standing wave field in which the particles have been focused to the center axis of the cylindrical flow channel

FIG. 4 illustrates a flow channel upon which a radial acoustic standing wave field is acting 400 according to one embodiment of the present invention. The flow channel upon which an ultrasonic radial acoustic standing wave is acting 400 includes a quartz flow channel 310, an aqueous saline solution 320, and particles 330. The quartz flow channel 310 contains the aqueous saline solution 320, and the particles 330 are suspended in the aqueous saline solution 320.

In operation, the aqueous saline solution 320, in which the particles 330 are suspended, flows through the quartz flow channel 310. The radial acoustic standing wave field, produced by vibrating the quartz flow channel 310 at a resonant frequency, directs acoustic waves from the cylindrical quartz flow channel 310 radially inward such that all of the particles 330 are focused to the center axis of the cylindrical quartz flow channel 310. Thus, the particles 330 flow into, through, and out of the quartz flow channel 310 with uniformity as to where they are located within the quartz flow channel 310, but without uniformity as to the intervals at which they exit from the quartz flow channel 310.

Vibrating the quartz flow channel 310 has a further advantage—the extended source formed by the flow channel structure as the source aperture translates into longer residence times of the particles 330 within the acoustic positioning field. The longer residence times allow for the use of lower pressure levels to drive the acoustic focusing field, which alleviates the problem associated with cavitation in an ultrasonic field that could damage fragile particles 330.

Figure 5:
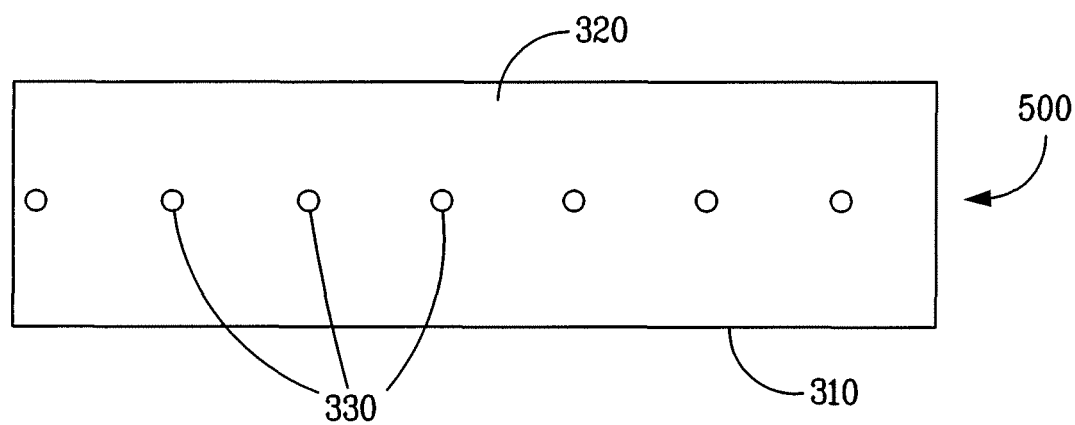
FIG. 5 illustrates a flow channel that has been exposed to a radial acoustic standing wave field and an axial acoustic standing wave field, in which the particles have been focused to the center axis of the cylindrical flow channel and are uniformly spaced.

FIG. 5 illustrates a flow channel upon which both a radial acoustic standing wave field and an axial acoustic standing wave field are acting 500 according to one embodiment of the present invention. The flow channel upon which both an ultrasonic radial acoustic standing wave and an ultrasonic axial acoustic standing wave field are acting 500 includes a quartz flow channel 310, an aqueous saline solution 320, and particles 330. The quartz flow channel 310 contains the aqueous saline solution 320, and the particles 330 are suspended in the aqueous saline solution 320.

In operation, the aqueous saline solution 320, in which the particles 330 are suspended, flows through the quartz flow channel 310. The radial acoustic standing wave field, produced by vibrating the quartz flow channel 310 at a resonant frequency, directs acoustic waves from the cylindrical quartz flow channel 310 radially inward such that all of the particles 330 are focused to the center axis of the cylindrical quartz flow channel 310. Thus, the particles 330 are no longer randomly positioned throughout the aqueous saline solution 320 in the quartz flow channel 310.

Further, the axial acoustic standing wave field, produced by a transducer at one end of the quartz flow channel 310, directs acoustic waves parallel to the axis of the cylindrical quartz flow channel 310. If particles 330 are more compressible and less dense than the surrounding fluid 320, they are driven to pressure anti-nodes along the center axis of the cylindrical quartz flow channel 310—acoustic traps. However, if particles 330 are denser and less compressible than the surrounding fluid 320, they are driven to pressure nodes along the center axis of the cylindrical quartz flow channel 310—more acoustic traps. The overall spacing of these particles 330 is therefore one half wavelength—on the order of between 100-1000 µm (though if these flow cells are used prior to hydrodynamic focusing, this spacing would increase slightly). Thus, the particles 330 flow into, through, and out of the quartz flow channel 310 with uniformity as to where they are located within and the intervals at which they exit from the quartz flow channel 310.

In the alternative, the quartz flow channel 310 may be made of a material other than quartz, such as glass or plastic. The overall spacing between the particles 330 may be other than 100-1000 pm, though it must be of such a distance as to be both viably analyzed and sorted at a rate comparable to or faster than current technologies.

Figure 6:
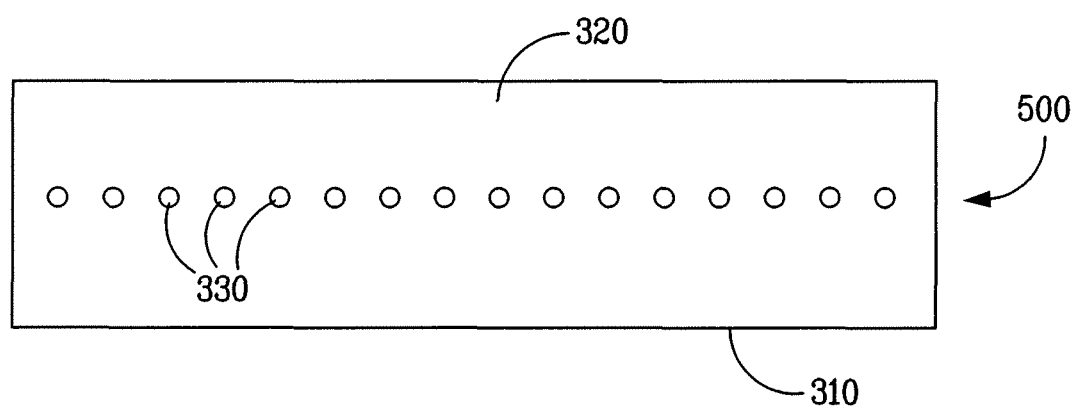
FIG. 6 illustrates a flow channel that has been exposed to a radial acoustic standing wave field, an axial acoustic standing wave field, and a non-uniform electric field, in which the particles have been focused to the center axis of the cylindrical flow channel and are more narrowly uniformly spaced than those shown in FIG. 5.

FIG. 6 illustrates a flow channel upon which a radial acoustic standing wave field, an axial acoustic standing wave field, and a non-uniform electric field are acting 600 according to one embodiment of the present invention. The flow channel upon which a radial acoustic standing wave field, an axial acoustic standing wave field, and a non-uniform electric field are acting 600 includes a quartz flow channel 310, an aqueous saline solution 320, and particles 330. The quartz flow channel 310 contains the aqueous saline solution 320, and the particles 330 are suspended in the aqueous saline solution 320.

In operation, the aqueous saline solution 320, in which the particles 330 are suspended, flows through the quartz flow channel 310. The radial acoustic standing wave field, produced by vibrating the quartz flow channel 310 at a resonant frequency, directs acoustic waves from the cylindrical quartz flow channel 310 radially inward such that all of the particles 330 are focused to the center axis of the cylindrical quartz flow channel 310. Thus, the particles 330 are no longer randomly positioned throughout the aqueous saline solution 320 in the quartz flow channel 310.

Further, the axial acoustic standing wave field, produced by a transducer at one end of the quartz flow channel 310, directs acoustic waves parallel to the axis of the cylindrical quartz flow channel 310. If particles 330 are more compressible and less dense than the surrounding fluid 320, they are driven to pressure anti-nodes along the center axis of the cylindrical quartz flow channel 310—acoustic traps. However, if particles 330 are denser and less compressible than the surrounding fluid 320, they are driven to pressure nodes along the center axis of the cylindrical quartz flow channel 310—more acoustic traps.

The particles 330 and the aqueous saline solution 320 in the quartz flow channel 310 are also exposed to a non-uniform electric field, which induces dielectrophoresis. The electric field is driven at the same frequency as the ultrasonic field, adding further driving force to position the particles 330 uniformly along the center axis of the cylindrical quartz flow channel 310. The combination of the axial acoustic standing wave field and the dielectrophoretic field allow for finer positioning of the particles 330 along the center axis of the cylindrical quartz flow channel 310, allowing for smaller uniform distances between particles 330 on the order of between 1-100 μm (though if these flow cells are used prior to hydrodynamic focusing, this spacing would increase slightly). Thus, the particles 330 flow into, through, and out of the quartz flow channel 310 with uniformity as to where they are located within and the intervals at which they exit from the quartz flow channel 310.

In the alternative, the quartz flow channel 310 may be made of a material other than quartz, such as glass or plastic. The overall spacing between the particles 330 may be other than 1-100 μm, though it must be of such a distance as to be viably analyzed and sorted at a rate comparable to or faster than current technologies.

Figure 7:
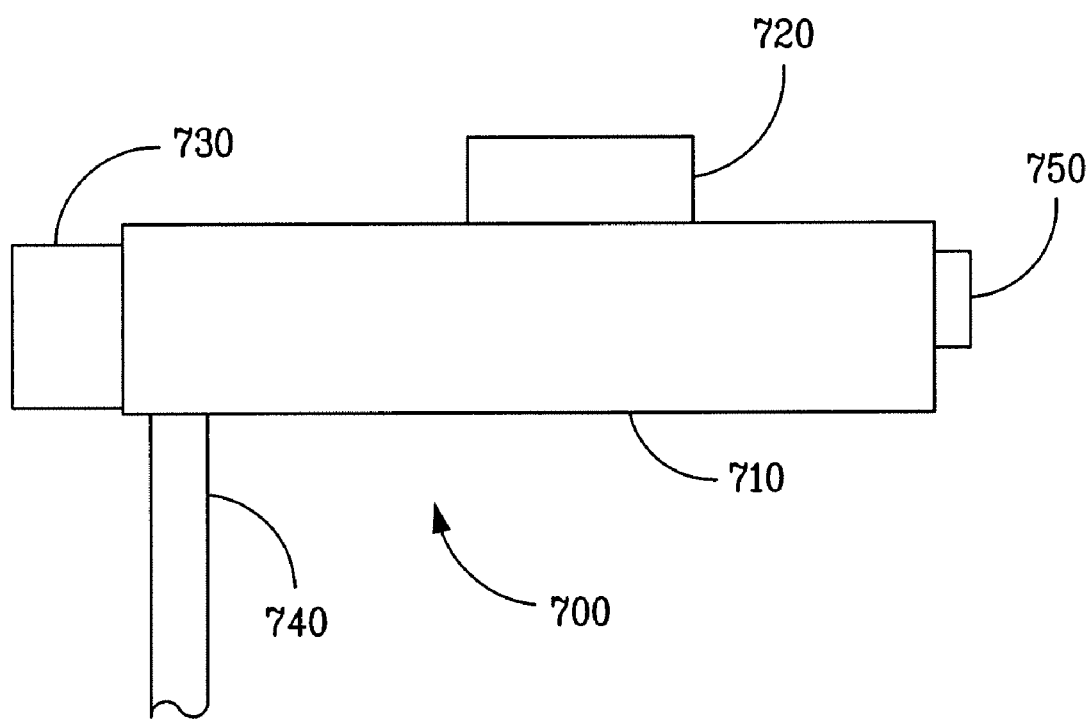
FIG. 7 illustrates a block diagram of the flow channel when two acoustic standing wave fields are in use.

FIG. 7 illustrates a block diagram of the flow channel assembly 700 according to an embodiment of the present invention. The flow channel assembly 700 of FIG. 7 includes a flow channel tube 710, a radial wave transducer 720, an axial wave transducer 730, an inlet tube 740, and an outlet port 750.

The radial wave transducer 720 is in contact with the flow channel tube 710 in such a manner that the vibrations of the radial wave transducer 720 cause the cylindrical walls of the flow channel tube 710 to vibrate in resonance. The axial wave transducer 730 is in contact with the flow channel tube 710 in such a manner that the vibrations of the axial wave transducer 730 cause an axial acoustic standing wave field to form that runs parallel to the center axis of the flow channel tube 710. The inlet tube 740 is attached to the flow channel tube 710 such that the flow stream of particles 330 suspended in an aqueous saline solution 320 flows from the inlet tube 740 into the flow channel tube 710. The outlet port 750 is attached to the flow channel tube 710 such that the flow stream of particles 330 suspended in an aqueous saline solution 320 flows out from the flow channel tube 710 through the outlet port 750.

In operation, the flow stream of particles 330 suspended in an aqueous saline solution 320 flows from the inlet tube 740 into the flow channel tube 710, which is made of quartz. While in the flow channel tube, the radial wave transducer 720, which is driven with a piezoelectric source, vibrates against the flow channel tube 710, causing the flow channel tube 710 to vibrate in resonance, which in turn causes a radial acoustic standing wave field to form inside the flow channel tube 710. At the same time, the axial wave transducer 730, which is driven with a piezoelectric source, vibrates against the flow channel tube 710, causing an axial acoustic standing wave field to form that runs parallel to the center axis of the flow channel tube 710. In combination, these wave fields focus and drive the particles 330 to half-wavelength spaced nodes and anti-nodes running along the center axis of the flow channel tube 710. The flow stream of particles 330 suspended in an aqueous saline solution 320, where the particles 330 are located at half-wavelength spaced nodes and anti-nodes running along the center axis of the flow channel tube 710 then exits the flow channel tube 710 through the outlet port 750.

In the alternative, the solution could be something other than an aqueous saline solution. The acoustic standing wave fields may also be other than acoustic wave fields, such as magnetic field, electric fields, gravitational fields, and optical fields. The flow channel may be a non-cylindrical shape, with multiple axial acoustic standing wave fields driving the particles to specific positions. The flow channel tube 710 may be a material other than quartz, such as glass or plastic.

Figure 8:
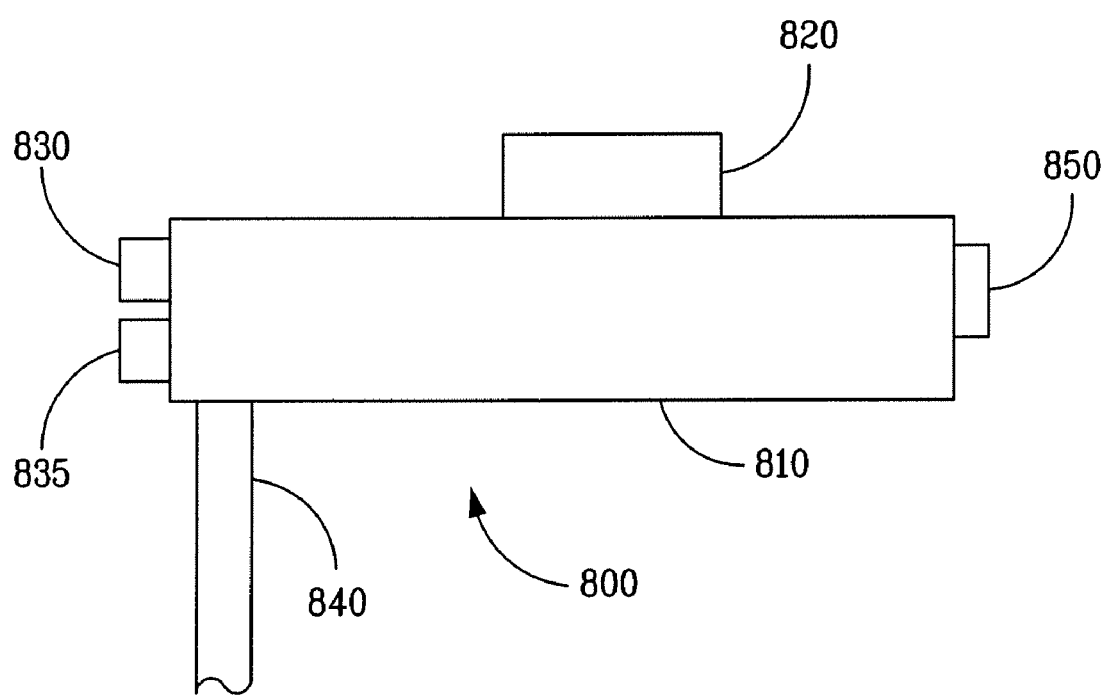
FIG. 8 illustrates a block diagram of the flow channel when two acoustic standing wave fields and a non-uniform electric field are in use.

FIG. 8 illustrates a block diagram of the flow channel assembly 800 according to one embodiment of the present invention. The flow channel assembly 800 of FIG. 8 includes a flow channel tube 810, a radial wave transducer 820, an axial wave transducer 830, a non-uniform active electrode surface 835, an inlet tube 840, and an outlet port 850.

The radial wave transducer 820 is in contact with the flow channel tube 810 in such a manner that the vibrations of the radial wave transducer 820 cause the cylindrical walls of the flow channel tube 710 to vibrate in resonance. The axial wave transducer 830 is in contact with the flow channel tube 810 in such a manner that the vibrations of the axial wave transducer 830 cause an axial acoustic standing wave field to form that runs parallel to the center axis of the flow channel tube 810. The non-uniform active electrode surface 835 is positioned at the axial wave transducer 830/aqueous saline solution 320 interface. The inlet tube 840 is attached to the flow channel tube 810 such that the flow stream of particles 330 suspended in an aqueous saline solution 320 flows from the inlet tube 840 into the flow channel tube 810. The outlet port 850 is attached to the flow channel tube 810 such that the flow stream of particles 330 suspended in an aqueous saline solution 320 flows out from the flow channel tube 810 through the outlet port 850.

In operation, the flow stream of particles 330 suspended in an aqueous saline solution 320 flows from the inlet tube 840 into the flow channel tube 810, which is made of quartz. While in the flow channel tube, the radial wave transducer 820, which is driven with a piezoelectric source, vibrates against the flow channel tube 810, causing the flow channel tube 810 to vibrate in resonance, which in turn causes a radial acoustic standing wave field to form inside the flow channel tube 810. At the same time, the axial wave transducer 830, which is driven with a piezoelectric source, vibrates against the flow channel tube 810, causing an axial acoustic standing wave field to form that runs parallel to the center axis of the flow channel tube 810. Concurrently, the non-uniform active electrode surface 835 creates the necessary field gradient for dielectrophoresis, driven at the same frequency as the ultrasonic field. In combination, these fields focus and drive the particles 330 to half-wavelength spaced nodes and anti-nodes running along the center axis of the flow channel tube 810. The flow stream of particles 330 suspended in an aqueous saline solution 320, where the particles 330 are located at half-wavelength spaced nodes and anti-nodes running along the center axis of the flow channel tube 810 then exits the flow channel tube 810 through the outlet port 850.

In the alternative, the solution could be something other than an aqueous saline solution. The acoustic standing wave fields may also be other than acoustic wave fields, such as magnetic field, electric fields, gravitational fields, and optical fields. The flow channel may be a non-cylindrical shape, with multiple axial acoustic standing wave fields driving the particles to certain positions. The flow channel tube 810 may be a material other than quartz, such as glass or plastic.

Figure 9:
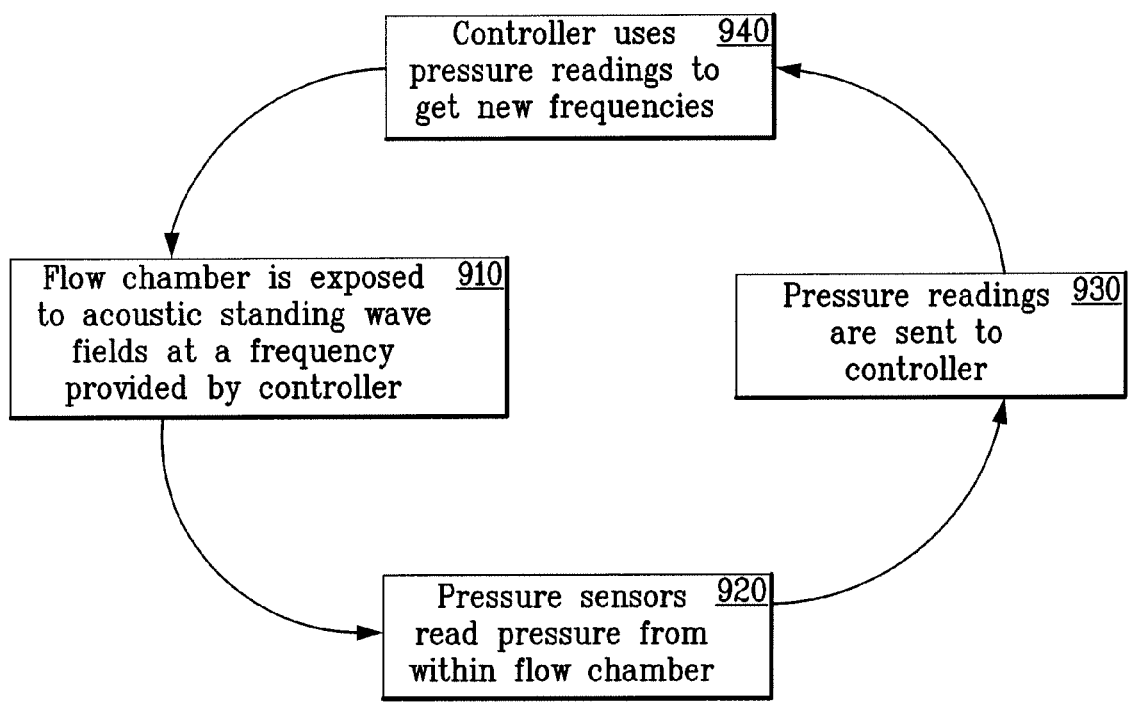
FIG. 9 illustrates a flow chart of a feedback loop that corrects the frequency of the acoustic standing waves for changes in pressure/temperature.

FIG. 9 illustrates a flow chart of a feedback loop 900 that corrects the frequency of the acoustic standing waves for changes in pressure/temperature according to one embodiment of the present invention. The feedback loop 900 begins with the step of exposing the flow channel to a radial acoustic standing wave fields at a frequency provided by a controller 910 to create a resonant vibration in the flow channel tube 710. Then, the step of reading pressure from within the flow cell tube with a pressure sensor 920 is performed to track temperature changes (and thus pressure changes) in the system. These temperature and pressure changes lead to changes in properties of the materials involved, such as changes in sound speed in fluid within the flow channel tube 710. Next, the step of sending the pressure readings to the controller 930 occurs, where the controller performs the step of using the pressure readings to provide a new frequency 940 to keep the flow channel tube 710 vibrating in resonance. The transducer and flow channel structure are chosen such that there is ample bandwidth to compensate for large temperature changes in the environment. The step of using the pressure readings to provide a new frequency 940 leads back to the original step of exposing the flow channel to a radial acoustic standing wave fields at a frequency provided by a controller 910 to create a resonant vibration in the flow channel tube 710, completing the feedback loop 900.

The controller may be one of a person, a mechanical device, an electric circuit, or a computer program. The sensor may be a temperature sensor as opposed to a pressure sensor.

One or more embodiments of the present invention, which focuses and uniformly spaces particles in a flow cytometer, greatly reduces the wasted time and effort dealing with stochastically arriving particles. The no longer uncertain positions of the particles in the flow stream avoid empty droplets, droplets with multiple particles, and particles at the break-off point between one droplet and another, all of which avoid aborted sorting events which greatly increase the overall sort rate. Further, the focusing of the particles allows larger particle to be sorted without increasing the size of the flow channel because there is less of a chance of the large particles to clog the flow channel. The smaller diameter flow channel leads to less turbulence, allowing for a higher linear velocity of the flow stream. One or more embodiments of the present invention assure predictable arrival of particles, allowing accurate high speed sorting of large particles.

In all embodiments of the present invention, all ranges are inclusive and combinable. All numerical amounts are understood to be modified by the word "about" unless otherwise specifically indicated.

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

Whereas particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of uniformly spacing particles in an open flowing system comprising:
    a) suspending particles in an elongated fluid filled cavity and flowing said fluid;
    b) exposing said cavity to an axial acoustic standing wave field parallel to the direction of flow, wherein said axial acoustic standing wave field drives said particles to nodal and anti-nodal positions along the center axis of said cavity to result in uniformly spaced particles; and
    c) focusing said particles to the center axis of said cavity.

2. The method of claim 1, wherein the focusing of said particles occurs by means of hydrodynamic focusing, acoustic focusing, a magnetic field, an electric field, a gravitational field, an optical field, or combinations thereof.

3. The method of claim 2, wherein the focusing of said particles occurs by means of hydrodynamic focusing.

4. The method of claim 1 further including exposing said cavity to a non-uniform dielectric-inducing electric field, wherein said electric field controls the distance between the uniformly spaced particles.

5. The method of claim 4, wherein said non-uniform dielectric-inducing electric field is a created by a lead zirconate titanate transducer having a nonuniform active electrode surface at the transducer/fluid interface.

6. The method of claim 1, wherein the particles are focused to the center axis of the cavity prior to exposure to the axial acoustic standing wave field.

7. The method of claim 1, wherein said axial acoustic standing wave field is created by a piezoelectric source.

8. The method of claim 1, wherein said fluid is a saline solution.

9. The method of claim 1, wherein said cavity in a shaft made of glass, quartz, or combinations thereof.

10. The method of claim 1, further including:
    sensing changes in pressure inside said cavity, wherein said sensing occurs in a pressure sensor; and adjusting the frequencies of said acoustic standing wave field to compensate for said pressure changes.

* * * * *